(12) United States Patent
Mason

(10) Patent No.: US 8,609,594 B2
(45) Date of Patent: Dec. 17, 2013

(54) CHLORINE DIOXIDE PRECURSOR AND METHODS OF USING SAME

(71) Applicant: Sabre Intellectual Property Holdings LLC, Slingerlands, NY (US)

(72) Inventor: John Y. Mason, Odessa, TX (US)

(73) Assignee: Sabre Intellectual Property Holdings LLC, Slingerlands, NY (US)

( * ) Notice: Subject to any disclaimer, the term of this patent is extended or adjusted under 35 U.S.C. 154(b) by 0 days.

(21) Appl. No.: 13/761,721

(22) Filed: Feb. 7, 2013

(65) Prior Publication Data

US 2013/0164388 A1 Jun. 27, 2013

Related U.S. Application Data

(63) Continuation of application No. 13/427,544, filed on Mar. 22, 2012.

(60) Provisional application No. 61/466,258, filed on Mar. 22, 2011.

(51) Int. Cl.
*C01B 11/02* (2006.01)
*A01N 59/00* (2006.01)
*C09K 8/52* (2006.01)

(52) U.S. Cl.
USPC ............ 507/267; 507/90; 507/103; 507/139; 507/140; 507/269; 507/277; 588/300; 252/182.32; 424/661; 423/478

(58) Field of Classification Search
USPC .......................................... 507/277; 588/300
See application file for complete search history.

(56) References Cited

U.S. PATENT DOCUMENTS

| | | | |
|---|---|---|---|
| 1,904,190 A * | 4/1933 | Becher .......................... | 423/478 |
| 3,789,108 A | 1/1974 | Rapson | |
| 4,086,329 A | 4/1978 | Cowley et al. | |
| 4,310,425 A | 1/1982 | Key et al. | |
| 4,465,658 A | 8/1984 | Fredette | |
| 4,473,115 A | 9/1984 | Oakes | |
| 4,482,459 A | 11/1984 | Shiver | |
| 4,627,969 A | 12/1986 | Fredette et al. | |
| 4,839,152 A | 6/1989 | Vella et al. | |
| 4,886,653 A | 12/1989 | Gasper et al. | |
| 4,945,992 A * | 8/1990 | Sacco ........................... | 166/310 |
| 4,964,466 A | 10/1990 | Williams et al. | |
| 5,016,714 A | 5/1991 | McCabe et al. | |
| 5,018,578 A | 5/1991 | El Rabbaa et al. | |
| 5,031,700 A | 7/1991 | McDougall et al. | |
| 5,204,081 A | 4/1993 | Mason et al. | |
| 5,227,031 A | 7/1993 | Sundblad | |
| 5,433,938 A * | 7/1995 | Wilson et al. .................. | 423/478 |
| 5,858,322 A | 1/1999 | Gray | |
| 6,468,479 B1 | 10/2002 | Mason et al. | |
| 6,711,830 B2 | 3/2004 | Hensley et al. | |
| 6,790,427 B2 | 9/2004 | Charles et al. | |
| 6,840,251 B2 * | 1/2005 | Gill et al. .................... | 134/22.12 |
| 6,981,549 B2 | 1/2006 | Morales et al. | |
| 7,131,495 B2 | 11/2006 | Hao et al. | |
| 7,514,005 B2 | 4/2009 | Browne et al. | |
| 7,578,968 B1 | 8/2009 | Nalepa et al. | |
| 7,615,518 B2 | 11/2009 | Perry et al. | |
| 7,678,280 B2 | 3/2010 | Mueller | |
| 7,712,534 B2 | 5/2010 | Bryant et al. | |
| 7,867,399 B2 | 1/2011 | Jones et al. | |
| 7,878,248 B2 | 2/2011 | Abad et al. | |
| 7,897,063 B1 | 3/2011 | Perry et al. | |
| 7,935,261 B2 | 5/2011 | Jones et al. | |
| 7,955,419 B2 | 6/2011 | Casella | |
| 7,964,101 B2 | 6/2011 | Slough et al. | |
| 8,083,935 B2 | 12/2011 | Eia | |
| 8,287,625 B2 | 10/2012 | Casella | |
| 2003/0203827 A1 | 10/2003 | Cooper et al. | |
| 2004/0224855 A1 | 11/2004 | Hao et al. | |
| 2007/0116637 A1 | 5/2007 | Woodruff et al. | |
| 2007/0295936 A1 | 12/2007 | Byrne et al. | |
| 2008/0003507 A1 | 1/2008 | Nanjundiah | |
| 2009/0062156 A1 | 3/2009 | Wilson et al. | |
| 2009/0229827 A1 | 9/2009 | Bryant et al. | |
| 2010/0059226 A1 | 3/2010 | Termine et al. | |
| 2010/0190666 A1 | 7/2010 | Ali et al. | |
| 2011/0005969 A1 | 1/2011 | Giffin | |
| 2011/0132815 A1 | 6/2011 | Angelilli et al. | |
| 2011/0137465 A1 | 6/2011 | Angelilli et al. | |
| 2011/0233136 A1 | 9/2011 | Enos et al. | |

FOREIGN PATENT DOCUMENTS

| | | |
|---|---|---|
| CA | 543589 | 7/1957 |
| CA | 825084 | 10/1969 |
| CA | 826577 | 11/1969 |
| CA | 1207269 | 7/1986 |
| GB | 2170220 A | 7/1986 |
| WO | 8501722 A1 | 4/1985 |

OTHER PUBLICATIONS

Search Report for related application PCT/US2012/030149 dated Jan. 2, 2013.

Vogt, Helmut et al., Chlorine Oxides and Chlorine Oxygen Acids, Ullman's Encyclopedia of Industrial Chemistry, vol. 8, pp. 623-684.

* cited by examiner

*Primary Examiner* — John J Figueroa

(74) *Attorney, Agent, or Firm* — Heslin Rothenberg Farley & Mesiti, P.C.; Alana M. Fuierer, Esq.

(57) ABSTRACT

According to one aspect of the invention, a method of converting an oxy halide salt into a halide dioxide in a reaction zone under certain conditions is provided. More specifically, the method includes generating chlorine dioxide from a stable composition comprising an oxy halide salt by introducing said composition to a reducing agent and minimum temperature within the reaction zone. According to another aspect of the invention, a composition for a stable chlorine dioxide precursor comprising an oxy halide salt is provided.

27 Claims, No Drawings

CHLORINE DIOXIDE PRECURSOR AND METHODS OF USING SAME

CROSS-REFERENCE TO RELATED APPLICATIONS

This application claims the benefit of priority from U.S. Provisional Application No. 61/466,258, filed Mar. 22, 2011 and U.S. Non-Provisional application Ser. No. 13/427,544, filed Mar. 22, 2012, both of which are incorporated herein by reference.

TECHNICAL FIELD

The claims recite a composition for a stable, chlorine dioxide precursor and method for using the same to generate chlorine dioxide for petroleum applications, such as, but not limited to, the use of chlorine dioxide in petroleum formations and high temperature gas or liquid streams. More particularly, the claims recite a composition comprising an oxy halide salt, (e.g., sodium chlorate) as a stable chlorine dioxide precursor for use in petroleum applications.

BACKGROUND

In the petroleum industry, numerous agents or contaminants can cause damage to or restriction of the production process. Examples of such contaminates can be high-molecular weight polymers (e.g. polyacrylamides, carboxymethylcellulose, hydroxyethylcellulose, CMC, HPG, and Zanthan), bacteria, sulfur, iron sulfide, hydrogen sulfide and similar compounds.

These contaminants can, in some cases, occur naturally in a formation or be present from prior human interactions. For example, bacteria are commonly introduced to a formation during drilling and workover (e.g. the repair or stimulation of an existing production well) operations. Similarly, during a fracturing process, bacteria are often introduced into the wellbore and forced deep into the formation. More specifically, polymers such as CMC, HPG, Zanthan, and polyacrilomides are added to the fracturing fluid to maintain the proppant in suspension and to reduce the friction of the fluid. Bacteria entrained within this fluid penetrate deep into the formation, and once frac pressure is released, become embedded within the strata in the same manner as the proppant deployed. Additionally, polymers can also be deposited within the formation, causing damage in their own right. Typically, conventional "breakers" are added to the fracturing fluid along with the polymer to prevent this problem, but damage to producing wells due to the incomplete destruction of polymers remains a common occurrence.

Many bacteria are facultative, that is they can exist in both aerobic or anaerobic conditions using either molecular oxygen or other oxygen sources to support their metabolic processes. For example, under the right conditions, facultative bacteria can use sulfate as an oxygen source and respire hydrogen sulfide, which is highly toxic to humans in addition to being corrosive to steel. Additionally, in a process known in the art as Microbiologically Induced Corrosion (MIC), bacteria will attach to a substrate, such as the wall of a pipe in the wellbore, and form a "biomass" shield around them. Underneath, the bacteria metabolize the substrate (e.g. a mixture of hydrocarbon and metallic iron) and respire hydrogen sulfide, resulting in the metal becoming severely corroded in the wellbore and, eventually, pipe failure and damage to downhole equipment. The respiration and presence of hydrogen sulfide also complicates the refining and transportation process, and attenuates the economic value of the produced hydrocarbon.

The traditional methods, when used alone to address these problems, have one or more drawbacks. For example, the present industry practice is to add conventional organic and inorganic biocides, such as quaternary ammonium compounds, chloramines, aldehydes, such as Gluteraldehyde, THPS and sodium hypochlorite, to fracturing fluids with other additives to control bacteria. The efficacy of these conventional biocides alone, however, can be minimal due to the type of bacteria that typically are found in hydrocarbon-bearing formations and petroleum production environments. More particularly, only a small percentage of these bacteria, which are often found in volcanic vents, geysers, and ancient tombs, are active at any one time; the remainder of the population is present in dormant and spore states. The aforementioned conventional biocides have no, or limited, effect on dormant and spore forming bacteria. Thus, while the active bacteria are killed to some extent, the inactive bacteria survive and thrive once they reach the environmental conditions found within the formation. Additionally, these biocides become inactivated when exposed to many of the components found in petroleum production formations. And, furthermore, microorganisms build resistance to these biocides, thus limiting their utility over time.

Chlorine dioxide, on the other hand, can inactivate or kill active, dormant and spore forming microorganisms. Unlike conventional biocides, microorganisms do not build a resistance to chlorine dioxide, and it has a low residual toxicity and produces benign end products. Chlorine dioxide is therefore an efficacious biocide, however certain applications have not been possible prior to the invention. For example, although chlorine dioxide can be applied directly to well fluids (for example, fracturing water) for disinfection, it can only be applied at a low dosage to prevent degradation of polymer(s) or other drag reduction additives.

Embodiments of this invention provide for a stable chlorine dioxide precursor additive. The chlorine dioxide precursor remains stable within, for example, well fluids (e.g. a fracturing fluid) or other fluid streams or systems until it enters a zone (e.g. within a subterranean formation) that satisfies certain conditions and reaches a minimum temperature of about 100° F.-110° F. One or more embodiments of the invention, which incorporate this chlorine dioxide precursor into a fracturing fluid, thus provide an in situ method for generating and using chlorine dioxide as a polymer oxidant and downhole biocide that does not deplete or attenuate the friction-reducing components of the fracturing fluid until the chlorine dioxide precursor is dispersed into the target zone of the subterranean, hydrocarbon-bearing formation. In these embodiments, the chlorine dioxide precursor reacts with components in the subterranean formation at a certain minimum temperature to form chlorine dioxide therein, which then acts as a polymer oxidant and downhole biocide.

The embodiments disclosed herein provide for results that cannot be accomplished with ex situ generated halogen dioxides, such as chlorine dioxide, or other halogen dioxide precursors alone, such as sodium chlorite. For example, chlorine dioxide cannot be added to well fluids (e.g. fracturing fluid) at high concentrations prior to injection into the wellbore because the chlorine dioxide will prematurely oxidize the polymers and friction-control additives within the fracturing fluid. Similarly, sodium chlorite, sometimes referred to as "stabilized chlorine dioxide," is limited in that it immediately begins to react with weak acids and other components of the fracturing fluids at ambient temperatures, thereby generating chlorine dioxide too soon, which in turn will prematurely oxidize the polymers and friction-control additives within the fracturing fluid. By contrast, embodiments of the present invention remain generally stable until exposed to a minimum temperature and reducing agents (e.g., contaminants) located within a subterranean formation or otherwise provided in a target reaction zone (i.e. high temperature gas or liquid streams such as, for example, in a pipeline).

Thus, embodiments of the invention provide for, inter alia, a composition that is stable under ambient conditions within a fluid stream or system (for example, the well fluids applied during drilling, completion, workover and fracturing operations), but subsequently reacts within a target reaction zone under specified conditions to produce a halide oxide that is capable of 1) degrading polymers within the target zone (i.e. the subterranean formation); 2) reducing toxic and unwanted sulfur compounds within the target zone (i.e. the subterranean formation and hydrocarbon deposits), and 3) functioning as a biocide that kills or destroys bacteria in active, dormant and spore forms.

BRIEF DESCRIPTION OF THE INVENTION

One aspect of the invention includes a method for introducing an oxy halide salt into a zone wherein the oxy halide salt comes into contact with a reducing agent resulting in conversion of the oxy halide salt into a halide dioxide, comprising applying or injecting an oxy halide salt into a zone with a reducing agent under conditions in which all or a part of the oxy halide salt is converted into the halide dioxide.

Another aspect of the invention includes a method of reducing, inactivating, destroying, or eliminating one or more reduced sulfur compounds, comprising the steps of contacting the reduced sulfur compound with an oxy halide salt under conditions in which all or a part of the oxy halide salt is converted into the halide dioxide, thereby reducing, inactivating, destroying, or eliminating one or more reduced sulfur compounds.

In another aspect of the invention, a method for oxidizing one or more polymers, one or more reduced sulfur compounds or one or more reduced metals, comprises the steps of contacting the polymer, reduced sulfur compound or reduced metal with an oxy halide salt in a reaction zone under conditions in which all or a part of the oxy halide salt is converted into the halide dioxide, thereby oxidizing one or more polymers, one or more reduced sulfur compounds or one or more reduced metals.

Another aspect of the invention includes a method for inactivating, destroying or killing one or more microbes, comprising contacting the microbe with an oxy halide salt under conditions in which all or a part of the oxy halide salt is converted into the halide dioxide, thereby inactivating, destroying or killing one or more microbes.

DETAILED DESCRIPTION

The following terms as used herein have the following meanings

As used herein, a biocide, or bactericide, is a substance that inhibits, destroys or kills bacteria.

As used herein, free residual level or residual is the amount of oxidant in a fluid present and available for microbiological control at a given time after the oxidant has reacted with background impurities and contaminants in the fluid. Generally described in units of percentage or ppm.

As used herein, well fluid is any fluid used in any of the drilling, completion, work over, fracturing and production of subterranean oil and gas wells.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

For the purposes of promoting an understanding of the principles of the invention, reference will now be made to embodiments of the invention and specific language will be used to describe the same. It will nevertheless be understood that no limitation of the scope of the invention is thereby intended, and any alterations and further modifications in the described embodiments, and any further applications of the principles of the invention as illustrated therein as would normally occur to one skilled in the art to which the invention relates are contemplated an protected.

According to one or more embodiments of the invention, a halide dioxide, preferably chlorine dioxide, is generated in situ in a target reaction zone. According to one aspect of the invention, the target reaction zone is found within a hydrocarbon-bearing subterranean formation and is the zone within the formation where the target compounds, or contaminants, are located. The target zone may also comprise a hydrocarbon deposit, a petroleum deposit, a hydrocarbon or petroleum product formation, or a hydrocarbon or petroleum processing product or equipment. As used herein, the target compounds, or contaminants, are agents located within the target zone that have the potential or propensity to cause damage to or restriction of the petroleum production process, and include high-molecular weight polymers (e.g. polyacrylamides, carboxymethylcellulose, hydroxyethylcellulose, CMC, HPG, and Zanthan), microbes (e.g. anaerobic and aerobic bacteria), sulfur, iron sulfide, hydrogen sulfide and similar compounds.

In one or more embodiments, a composition comprises a stable, halogen dioxide precursor concentrate that does not react with the target compounds prior to entering the target reaction zone within the subterranean formation. The halogen dioxide precursor comprises an oxy halide salt, such as sodium chlorate, in solution at a concentration up to about 50% by weight, preferably about 5% to 40% by weight. Although the embodiments and examples disclosed herein refer to sodium chlorate as the oxy halide salt, one of ordinary skill in the art would recognize that other oxy halide salts containing a chlorine in the plus five valence or oxidation state, such as potassium chlorate, calcium chlorate, or magnesium chlorate, would fall within the embodiments of this invention. The stable precursor concentrate will typically be added to a fluid stream (e.g. well fluid) at concentrations ranging from about 100 to 10,000 mg/l.

Although not required, in one or more embodiments, the composition or concentrate comprising the stable chlorine dioxide precursor further comprises additives selected to benefit the type of treatment that is targeted. For example, in certain embodiments, the halogen dioxide precursor further comprises and is premixed with additives, preferably chelants or weak acids, such as citric acid, or wetting agents such as ethylene glycol monobutyl ether. More specifically, in one embodiment, the composition comprises up to about 40% by weight sodium chlorate, up to 20% by weight of a chelating agent, and up to about 10% by weight of a surface active agent. In other embodiments, the composition comprises an aqueous solution of an oxy halide salt and a weak acid, wherein the concentration of the oxy halide salt is between about 5% and 40% and the concentration of the weak acid is between about 5% and 20%. In still other embodiments, more specifically in embodiments wherein the target reaction zone alone supplies a sufficient amount hydrogen ions to allow for the generation of chlorine dioxide, the stable precursor composition does not include any chelating agent.

Because the target compounds within the target zone react with the stable precursor to form a halogen dioxide, preferably chlorine dioxide, as an end-product of the reaction, a free residual of said halide oxide is generated in situ and is available to oxidize other compounds, function as a biocide and control or inactivate microbes located either within or around the target zone. Therefore, in one or more embodiments of this invention, no ex situ generator or process is required to generate chlorine dioxide for injection into the subterranean formation and/or gas or liquid streams in order to destroy or reduce polymers, sulfur, reduced sulfur compounds, phenols and other compounds, although it remains optional.

More specifically, in one or more embodiments, the premixed composition, or concentrate, comprising said halogen dioxide precursor is stable and not reactive in solutions of polymer, sulfides, and/or weak acids at ambient conditions and temperatures, and more specifically is stable in solutions of polymer, sulfides, and/or weak acids at temperatures in the range of less than about 90° F. to 110° F., and more preferably does not react to form chlorine dioxide until the temperature reaches or exceeds about 110° F. to 115° F. The composition is stable at ambient temperatures in, for example, drilling, fracturing, completion, and operational well fluids, including but not limited to drilling muds, fracturing fluids, produced or fresh water, or blends thereof. In still other embodiments of the invention, the composition or concentrate also remains stable at temperatures in the range of less than about 90° F. to 110° F. when premixed with a low concentration of a strong acid, such as hydrochloric or hydrofluoric acid, wherein the concentration of the strong acid can be in the range of about 0.1% to 2%, more preferably 0.2% to 0.5%. Both the selection and concentration of a weak or strong acid is determined by the concentration at which said acid will not react to form chlorine dioxide when it is mixed directly with the oxy halide salt at temperatures in the range of less than about 90° F. to 110° F.

The composition comprising the stable halogen dioxide precursor therefore remains stable until it reaches a target reaction zone, wherein the composition is then exposed to temperatures of at least about 90° F. to 110° F., and preferably reaches or exceeds about 110° F. to 115° F., and wherein the composition is further exposed or introduced to at least one of or a combination of one or more of the following: a hydrocarbon containing formation, reduced sulfur compounds, elemental sulfur, sulfite, polymer, biomass (i.e. microbes or bacteria), reduced metal ions, and other easily oxidized organic and inorganic compounds. For example, in one or more embodiments, the reduced sulfur compounds are present in a target reaction zone within a subterranean geological formation or material that contains one or more solid, liquid, or gaseous hydrocarbons, or a hydrocarbon deposit, a petroleum deposit, a hydrocarbon or petroleum product formation, or a hydrocarbon or petroleum processing product or equipment. In another embodiment, microbes and reduced sulfur compounds are present in a target reaction zone within a petroleum processing piece of equipment. In still another embodiment, polymers and reduced sulfur compounds are present in a target reaction zone within the fractures of hydrocarbon-bearing subterranean formation.

Embodiments of the present invention also provide that the concentrate or composition comprising said halogen dioxide precursor is either added to or premixed with a fluid stream, for example a fluid stream being injected into a subterranean wellbore, wherein said fluid stream may include other additives, such as friction reducers, wetting agents, polymers, corrosion inhibitors, sand, proppants, biocides, breakers and other chemicals and wherein the chlorine dioxide precursor is and remains stable in the presence of these additives until it reaches the target reaction zone. Once it reaches the target reaction zone, the halogen dioxide precursor is introduced to a high temperature liquid or gas stream that contains one or more of sulfides, reduced sulfur compounds, polymers, microbial matter or other target compounds. More specifically, the high temperature fluid or gas stream is at or brought up to temperatures above about 90° F. to 115° F., and preferably above about 110° F. to 115° F. When the halogen dioxide precursor solution reaches the target reaction zone within the formation that contains the conditions set forth above, said precursor composition will react spontaneously to form halogen dioxide (e.g., chlorine dioxide) in said zone. The in situ generated halogen dioxide will then destroy polymers and other target compounds, such as reduced sulfur compounds, biomass (e.g. microbes, bacteria), sulfur, phenols, either within, around or after said zone, such that the halogen dioxide formation reaction that initiates in said zone will consume the contaminants.

In one embodiment, said stable composition or concentrate is premixed offsite and is then transported to the work site. In other embodiments, for example during a hydraulic fracturing operation, said composition can be premixed at the work site in one of the frac tanks or in the blender. The premixed concentrate comprising the stable chlorine dioxide precursor and other additives is then injected into the process stream via a chemical injector system and/or other method that is known to those skilled in the art.

The dosage rate and concentration of the composition comprising the stable precursor is calculated based on the quantity of chlorine dioxide, or other halogen oxide, that needs to be generated and/or the amount of contaminants that need to be consumed. More specifically, the dosage rate and concentration can be determined based on the nature of the treatment, the characteristics of the fluid or gas stream, the characteristics of the subterranean formation (if applicable), and the contaminants contained therein, as would be determined by those skilled in the art. For example, and in one embodiment, the application ratio to eliminate reduced sulfur compounds and oxidate reduced metal ions is approximately 2.5 to 5:1 chlorine dioxide precursor to target compound by weight.

When chlorine dioxide or other halogen dioxides are added directly to well fluids (i.e. fracturing fluids) or other fluid streams, they can initially react with dissolved organic and inorganic compounds in the water, thus depleting the amount of free residual available as a biocide and for other intended treatment purposes. Therefore, in one or more embodiments of the present invention, it will be necessary to add an excess of the stable precursor in order to produce a free residual of the halogen dioxide sufficient to achieve the desired bacterial control and/or oxidation of complex organics. In yet another embodiment, if instant biocidal control is desired or required, the stable precursor of the present invention may be incorporated into a water or fluid stream that has already has been dosed with a generated solution of chlorine dioxide or other biocidal agent. More specifically, and by way of example only, chlorine dioxide concentrations of 10 to 20 mg/l or less do not impact the performance of the additives, such polymer(s) or other drag reduction additives, in fracturing fluids. Therefore, in certain embodiments, the composition comprising the stable precursor can be added to raw fracturing water that contains a sufficient residual of chlorine dioxide, for example from about 0.02 to 5 mg/l, and preferably from about 1-2 mg/l, to provide primary disinfection of the raw water without prematurely depleting or effecting the performance of the other additives. The addition of this low-residual, generated chlorine dioxide provides primary disinfection and inhibits or prevents biofouling of the mixing and pumping equipment. As described herein, and in accordance with the invention, the composition comprising the stable precursor will not provide appreciable biocidal control until activation, i.e. when it is introduced to the appropriate conditions within the reaction zone, including one or more reducing agents and fluid temperatures at a minimum of about 90° F. to 110° F., and preferably at or above about 110° F. to 115° F.

Although the embodiments disclosed hereinabove often refer to the target reaction zone as located within a subterranean formation, in accordance with alternate embodiments that are within the scope of the invention, the reaction zone can also equipment, a pipeline or vessel for extracting, processing, refining, transporting or storage of hydrocarbons. In order to oxidize contaminants in a fluid or gas stream in accordance with the invention in these embodiments, a stable precursor composition or concentrate will comprise up to about 40% of a oxy halide salt, preferably sodium chlorate and may also comprise up to about 20% by weight of a chelating agent. The composition is then introduced via the fluid or gas stream to an environment with a minimum temperature of about 90° F. to 100° F., ideally over about 100° F., and more preferably over about 110° F. to 115° F., wherein said fluid or gas stream further comprises contaminants such as reduced metal ions, biomass, reduced sulfur compounds, or other reduced organics such as phenols or tertiary alcohols or amines.

The inventor has also found that, due to the oxidation of sulfides and other contaminants, the generation of chlorine dioxide within a formation in accordance with this invention will affect the affinity of hydrocarbons to non-hydrocarbons, such that the embodiments disclosed herein result in hydrocarbons being released from the subterranean formation in amounts greater than would have occurred without the generation of chlorine dioxide within the formation. More specifically, in situ generated chlorine dioxide via the stable precursor composition disclosed herein effectuates the removal of hydrocarbons from subterranean formation material, while other oxidants such as hydrogen peroxide, sodium persulfate, sodium peroxide, sodium chlorite, and sodium hypochlorite do not.

Although the above description has focused on the use of in situ generation of chlorine dioxide via the stable precursor composition disclosed herein to effectuate the removal of hydrocarbons during oil and gas production, the stable chlorine dioxide precursor and method for using the same in accordance with this invention can also be applied and used in connection with the production of other petroleum products.

EXAMPLES

Example 1

This example illustrates a representative reaction in which chlorine dioxide is formed from a precursor. A chlorine dioxide precursor reacts with reduced contaminant to form chlorine dioxide by gaining an electron from the contaminant.

$$ClO_3^- + Rx \rightarrow ClO_2 + RxO^-;$$

where Rx is the reducing agent providing an electron in the reduction of chlorate to chlorine dioxide.

The formed chlorine dioxide competes with the stable precursor in the oxidation of the contaminants, and as a reactive free radical oxidizes additional compounds that are non reactive with the precursor. Neither chlorine dioxide nor chlorate react via electrophilic substitution and do not thus form chlorinated organic compounds. One known pathway for chlorate to form chlorine is in the absence of a reducing agent under strong acid conditions, as represented by the following reaction:

$$ClO_3^- + 2HCl \rightarrow ClO_2 + \tfrac{1}{2}Cl_2 + H_2O$$

No strong acids are present in the media during the application of the present invention and reducing agents are always present during the chlorine dioxide formation. Mixture of the chlorine dioxide precursor with a strong acid is generally avoided to prevent chlorination and corrosive effects from the resultant chlorine.

Example 2

A solution was made up of 10% by weight of sodium chlorate, 10% citric acid, and 0.15% hydrochloric acid. Samples of the solution were stored at 80° F., 90° F., 100° F., 110° F., 120° F. and 150° F. and monitored for sixty days using spectrophotometric analysis for the presence of chlorine dioxide. At no time during the test period was there a physical change in the solution, evidence of off-gassing or evidence of chlorine dioxide production. At the end of the observation period the samples were analyzed for sodium chlorate. No significant change in the concentration was observed. The foregoing study demonstrates that solutions of an oxy halide salt can be formulated with weak acids or low concentrations of strong acids (e.g., hydrochloric acid) without the resultant formation of chlorine dioxide that would prevent their transportation under DOT regulations, or degradation of the product within a normal shelf life period.

Example 3

Identical examples of the solution used in Example 2 were mixed with the addition of 0.5% Iron Sulfide. Samples of the final solution were stored at 80° F., 90° F., 100° F., 110° F., 120° F. and 150° F. and monitored for sixty days using spectrophotometric analysis for the presence of chlorine dioxide. At temperatures of up to 110° F., no evidence of reaction or chlorine dioxide formation was observed and hydrogen sulfide gas was evolved into the head space of the samples. At the end of the sixty day cycle chlorate analysis indicated no significant change. The 120° F. samples showed a slow degradation of the hydrogen sulfide and yellowing of the solution over a 48 hour period. After 48 hours there was no remaining sulfide within the sample and there was a slight residual of 8-10 ppm chlorine dioxide. The 150° F. sample immediately yellowed and consumed the iron sulfide without a release of hydrogen sulfide upon addition and formed a slight 10 to 15 ppm residual of chlorine dioxide. Once iron sulfide was consumed formation of chlorine dioxide ceased. Additional aliquots of iron sulfide resulted in complete destruction of the sulfide and oxidation of the iron to the ferric state. Subsequent analysis of the residual chlorate revealed that chlorate was consumed by approximately a 2.7 chlorate to sulfide weight ratio. The foregoing study demonstrates that the stable chlorine precursor will react at typical production formation conditions to form chlorine dioxide and consume the target contaminants and form sufficient residual chlorine dioxide to kill, inactivate or destroy more stable or resilient contaminants such as bacteria and polymers.

Example 4

Identical examples of the solution used in Example 2 were mixed with the addition of 5% by weight ground up core material. The materials were sandstone and dolomite in nature, and contained approximately 10 mg/kg of iron sulfide. Samples of the final solution were stored at 80° F., 90° F., 100° F., 110° F., 120° F. and 150° F. and monitored for sixty days using spectrophotometric analysis for the presence of chlorine dioxide. At temperatures of up to 100° F., there was no evidence of reaction or chlorine dioxide formation, and hydrogen sulfide gas was evolved into the head space of the samples. At the end of the sixty day cycle, chlorate analysis indicated no significant change in chlorate concentration. The 110° F., 120° F. and 150° F. samples showed a slow degradation of the hydrogen sulfide and yellowing of the solution over a 48 hour period. After 48 hours, there was no remaining sulfide within the sample and there was a slight residual of 8-10 ppm chlorine dioxide. The 150° F. sample immediately yellowed and consumed the iron sulfide without a release of hydrogen sulfide upon addition, and formed a slight 10 to 15 ppm residual of chlorine dioxide. Subsequent analysis of the residual chlorate revealed that chlorate was consumed by approximately a 3.2 chlorate to sulfide weight ratio. The foregoing study demonstrates that production zone material can provide sufficient reducing materials for the conversion of a precursor to chlorine dioxide to occur.

Example 5

In this example, a first flask contained a 0.5 percent solution of sodium sulfide. A second flask contained a solution of 10% sodium chlorate and 10% citric acid. A third flask contained a 5% solution of ferric (iron) sulfate. An inert gas stream purged gases from flask to flask through a gas train. Hydrochloric acid was added to the first flask to evolve hydrogen sulfide gas. The study was conducted at 100° F., 150° F., 175° F. and 200° F. At 100° F. and 150° F., no reaction was observed within the second flask and hydrogen sulfide reacted with the iron sulfate solution to form iron sulfide in the third flask. Some hydrogen sulfide vented from the third flask. At 175° F., iron sulfide was still formed in the third flask and some hydrogen sulfide vented, but to a much lesser extent. Flask 2 remained clear at the end of the study, but evolved some chlorine dioxide. At 200° F., no iron sulfide formed within the third flask or was vented from the gas train. The solution in flask 2 displayed evidence of chlorine dioxide formation and had a slight residual of chlorine dioxide of approximately 5 mg/l at the conclusion of the study the foregoing study demonstrates that an elevated temperature gas stream has sufficient reducing properties to trigger the conversion of precursor to chlorine dioxide, and that reducing agents within the contaminants can be used as the reductant (hydrogen sulfide) to trigger the conversion with sufficient halo dioxide to result in the elimination of the reductant.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What I claim is:

1. A method for generating chlorine dioxide, said method comprising the steps of:
    a) providing a single vessel;
    b) blending or mixing an oxy halide salt with an acid within the single vessel to form a pre-mixed composition, wherein the acid comprises a weak acid in the range of about 5% to about 20%, more preferably about 5% to about 10%, or a strong acid in the range of about 0.1% to about 2%, more preferably about 0.2% to about 0.5%;
    c) maintaining within said vessel a temperature below about 100° F, an absence of a reducing agent, or both, wherein; said pre-mixed composition is stable within the vessel and does not convert to a halide oxide;
    d) dispensing the premixed, stable composition from the single vessel; and
    e) introducing said pre-mixed, stable composition into a reaction zone under conditions in which all or a part of the oxy halide salt is converted into chlorine dioxide, wherein
    the anion component of the oxy halide salt comprises chlorate,
    and said conditions in the reaction zone comprise the presence of one or more reducing agents and a temperature greater than about 110° F.

2. The method of claim 1, wherein said reaction zone is selected from the group consisting of geological material that contains one or more solid, liquid, or gaseous hydrocarbons, a hydrocarbon deposit, a petroleum deposit, a hydrocarbon or petroleum product formation, and a hydrocarbon or petroleum processing product or equipment, or combinations thereof.

3. The method of claim 2, wherein the hydrocarbon or petroleum processing product or equipment is selected from the group consisting of one or more pieces of equipment for extracting, processing, or refining hydrocarbons, a pipeline for transporting hydrocarbons and a vessel for storage of hydrocarbons.

4. The method of claim 1, wherein the chlorine dioxide is sufficient to reduce, inactivate, destroy, or eliminate at least one or more reducing agents, polymers or microbes in the reaction zone.

5. The method of claim 1, wherein the one or more reducing agents are selected from the group consisting of elemental sulfur, reduced sulfur compounds, reduced metals, reduced organic compounds and mixtures thereof 6. The method of claim 1, wherein the reaction zone has a minimum temperature of about 110° F. to about 115° F.

7. The method of claim 1, wherein the temperature greater than about 110° F. or reducing agents are introduced when the oxy halide salt enters a hydrocarbon-bearing formation.

8. The method of claim 1, wherein the oxy halide salt is in an aqueous medium.

9. The method of claim 8, further comprising heating the aqueous medium to a minimum temperature of about 110° F. to about 115° F.

10. The method of claim 8, wherein the aqueous medium is blended or mixed with a free residual of chlorine dioxide in the range of about 0.02 mg/l to about 5 mg/l, preferably in the range of about 1 mg/l to about 2 mg/l, prior to the step of being introduced into the reaction zone.

11. The method of claim 1, wherein the weak acid comprises citric, lactic, formic, oxalic, ethanoic, acetic, or propanoic acid, or a mixture of one or more of said weak acids.

12. The method of claim 1, wherein the strong acid comprises hydrochloric or hydrofluoric acid.

13. The method of claim 1, wherein said vessel is selected from the group consisting of a tank, receptacle, reservoir and container containing said premixed, stable composition.

14. The method of claim 1, further comprising the step of transporting said pre-mixed, stable composition to a location near the reaction zone before or after step (d).

15. The method of claim 1 further comprising the step of filling a storage container with the pre-mixed, stable composition for future use after step (d).

16. A composition for generating chlorine dioxide comprising:
a pre-mixed, stable combination comprising an oxy halide salt, the anion component of the oxy halide salt comprising chlorate, and an acid selected from the group comprising a weak acid in the range of about 5% to about 20%, more preferably about 5% to about 10%, and a strong acid in the range of about 0.1% to about 2%, more preferably about 0.2% to about 0.5%, said combination excluding chlorine dioxide and stored in the absence of a reducing agent, or at a temperature below about 100° F., or both;
wherein the pre-mixed composition generates chlorine dioxide when introduced to or in the presence of one or more reducing agents in combination with a temperature greater than about 110° F.

17. The composition of claim 16, wherein the weak acid comprises citric, lactic, formic, oxalic, ethanoic, acetic, or propanoic acid, or a mixture of one or more of said weak acids.

18. The composition of claim 16, wherein the strong acid comprises hydrochloric or hydrofluoric acid.

19. The composition of claim 16, wherein the one or more reducing agents are selected from the group consisting of elemental sulfur, reduced sulfur compounds, reduced metals, reduced organic compounds and mixtures thereof.

20. The composition of claim 16, wherein the oxy halide salt is in an aqueous medium.

21. The composition of claim 16, wherein the composition further comprises a chelating, a wetting agent or a mixture thereof.

22. A vessel containing the stable composition of claim 16, wherein said vessel is selected from the group consisting of a tank, receptacle, reservoir and container.

23. A stable, aqueous solution comprising pre-mixed solution of an alkaline metal oxy halide salt, a weak acid and water, said solution stored at a temperature below about 100° F., or in the absence of a reducing agent, or both; wherein
the concentration of the alkaline metal oxy halide salt is between about 5% and 40%, the concentration of the weak acid is between about 5% and 20%, the concentration of chlorine dioxide within the solution is undetectable and the anion component of the oxy halide salt comprises chlorate;
and wherein the pre-mixed, stable solution forms chlorine dioxide when introduced to one or more reducing agents in combination with a temperature greater than about 110° F.

24. The solution of claim 23, wherein the one or more reducing agents are selected from the group consisting of elemental sulfur, reduced sulfur compounds, reduced metals, reduced organic compounds and mixtures thereof 25. The solution of claim 24, wherein the reduced metal comprises Fe(II).

26. The solution of claim 23, wherein the temperature greater than about 110° F. and reducing agents are introduced when the stable solution enters or comes in contact with a geological material comprising one or more solid, liquid, or gaseous hydrocarbons, a hydrocarbon deposit, a petroleum deposit, a hydrocarbon or petroleum product formation, or a hydrocarbon or petroleum processing product or equipment.

27. A vessel containing the stable solution of claim 23, wherein said vessel is selected from the group consisting of a tank, receptacle, reservoir and container.

* * * * *